United States Patent
Sasaki et al.

(10) Patent No.: US 9,393,082 B2
(45) Date of Patent: Jul. 19, 2016

(54) VISCOUS MATERIAL CONTAINER HAVING ANNULARLY CONTACTING PISTON

(71) Applicant: SHOFU INC., Kyoto-shi, Kyoto (JP)

(72) Inventors: Tsukasa Sasaki, Soka (JP); Ryouji Takei, Soka (JP); Toshiyuki Nakatsuka, Kyoto (JP); Katsuya Kimoto, Kyoto (JP); Hideto Kasaba, Kyoto (JP)

(73) Assignee: SHOFU, INC., Kyoto-Shi (JP)

( * ) Notice: Subject to any disclaimer, the term of this patent is extended or adjusted under 35 U.S.C. 154(b) by 0 days.

(21) Appl. No.: 14/224,180

(22) Filed: Mar. 25, 2014

(65) Prior Publication Data

US 2015/0090742 A1    Apr. 2, 2015

(30) Foreign Application Priority Data

Sep. 30, 2013  (JP) ................. 2013-205447

(51) Int. Cl.
 *B67D 7/60* (2010.01)
 *G01F 11/00* (2006.01)
 *A61C 5/06* (2006.01)
 *B05C 17/005* (2006.01)

(52) U.S. Cl.
 CPC .............. *A61C 5/062* (2013.01); *A61C 5/066* (2013.01); *B05C 17/00576* (2013.01)

(58) Field of Classification Search
 CPC ... A61C 5/062; A61C 5/066; B05C 17/00576
 USPC ............................. 222/386; 433/90
 See application file for complete search history.

(56) References Cited

U.S. PATENT DOCUMENTS

| | | | | |
|---|---|---|---|---|
| 5,707,234 A | * | 1/1998 | Bender | 433/90 |
| 5,848,894 A | * | 12/1998 | Rogers | 433/90 |
| 5,893,714 A | | 4/1999 | Arnold et al. | |
| 6,261,094 B1 | * | 7/2001 | Dragan | 433/90 |
| 6,379,152 B1 | * | 4/2002 | Dragan | 433/90 |
| 8,556,870 B2 | * | 10/2013 | Fundingsland et al. | 604/311 |
| 2002/0076671 A1 | * | 6/2002 | Evers et al. | 433/90 |
| 2004/0152041 A1 | * | 8/2004 | Metzbower | 433/90 |
| 2005/0147939 A1 | * | 7/2005 | Zumkeller | 433/90 |
| 2006/0204924 A1 | * | 9/2006 | Galehr et al. | 433/90 |
| 2012/0028217 A1 | * | 2/2012 | Spreizer | 433/90 |
| 2013/0134188 A1 | * | 5/2013 | Terakawa et al. | 222/386 |

FOREIGN PATENT DOCUMENTS

| | | |
|---|---|---|
| EP | 1147747 A2 | 10/2001 |
| EP | 1340472 A1 | 9/2003 |
| JP | 10-179608 | 7/1998 |
| KR | 10-0985728 B1 | 10/2010 |

OTHER PUBLICATIONS

European Search Report dated Feb. 10, 2015, 6 pages.

* cited by examiner

*Primary Examiner* — Patrick M Buechner
*Assistant Examiner* — Jeremy W Carroll
(74) *Attorney, Agent, or Firm* — Rankin, Hill & Clark LLP

(57) ABSTRACT

A viscous material container that makes it unlikely that air remains in a housing when a piston is inserted from an insertion port of the housing. A first section of the housing is formed with two groove portions communicating with a first passage to discharge air in the first passage when a piston is inserted from an insertion port. The two groove portions communicate with the insertion port, and extend along a first imaginary center line.

5 Claims, 4 Drawing Sheets

VISCOUS MATERIAL CONTAINER HAVING ANNULARLY CONTACTING PISTON

TECHNICAL FIELD

The present invention relates to a viscous material container configured to contain a viscous material and discharge an appropriate amount of the viscous material.

BACKGROUND ART

In treating a dental viscous material with a high viscosity such as a dental filling material, an artificial tooth material, and a tooth crown material in the dental field, a viscous material container such as a dental viscous material container that is a disposable container filled with the dental viscous material is used. The dental viscous material container is set onto a dedicated pushing device with a handle, and the handle of the pushing device is operated to discharge an appropriate amount of the dental viscous material from the dental viscous material container.

JP10-179608A describes an example of the viscous material container according to the related art. The viscous material container includes a housing including a first section, a second section, and a third section. The first section has an insertion port at an end thereof, and includes a first inner wall surface configured to surround a first passage extending along an imaginary center line from the insertion port and having a transverse sectional shape that is circular about the imaginary center line. The second section has a discharge port at an end thereof, and includes a second inner wall surface configured to surround a second passage extending from the discharge port. The third section is positioned between the first section and the second section, and includes a third inner wall surface configured to surround a third passage communicating with the first passage and the second passage. A piston is inserted into the first passage to push out a viscous material, which is contained in the first passage, from the discharge port through the second and third passages. As illustrated in FIG. 1 of JP10-179608A, the piston (13) includes: one seal ring (14) configured to contact the first inner wall surface as the piston is inserted in the first passage; and a pair of non-contact portions (15) configured not to contact the first inner wall surface as the piston is inserted in the first passage, located at both sides of the seal ring (14) in the direction of extension of the imaginary center line and having an outside diameter that is smaller than that of the seal ring (14). The pair of non-contact portions (15) of the piston (13) is shaped to be plane-symmetric with respect to an imaginary surface that includes the seal ring (14) and is orthogonal to the imaginary center line.

SUMMARY OF INVENTION

Technical Problem

In the structure described in JP10-179608A, however, air may remain in the housing when the piston is inserted from the insertion port of the housing. If air remains in the housing, air bubbles may mix into the viscous material when the viscous material is pushed out from the discharge port. In the dental field, in particular, intrusion of such air bubbles may change the apparent color of the viscous material or cause growth of bacteria from the air bubbles. In addition, the remaining air may reduce a resistive force exerted from inside the housing when the piston is pushed in. This may change a feel (tactile response) obtained when the piston is pushed in, and makes it difficult to control a force for pushing in the piston.

An object of the present invention is to provide a viscous material container that makes it unlikely that air remains in a housing when a piston is inserted from an insertion port of the housing.

Solution to Problem

The present invention is directed to a viscous material container including a housing and a piston. The housing includes a first section, a second section, and a third section. The first section has an insertion port at an end thereof, and includes a first inner wall surface configured to surround a first passage extending along a first imaginary center line from the insertion port and having a transverse sectional shape that is circular about the first imaginary center line. The second section has a discharge port at an end thereof, and includes a second inner wall surface configured to surround a second passage extending along a second imaginary center line from the discharge port and having a transverse sectional shape that is circular about the second imaginary center line. The second imaginary center line intersects the first imaginary center line. The third section is positioned between the first section and the second section, and includes a third inner wall surface configured to surround a third passage communicating with the first passage and the second passage. The piston is operable to move inside at least the first passage to push out a viscous material, which is contained in the first passage, from the discharge port through the second and third passages. The piston includes one annularly circular contact portion and a pair of non-contact portions. The one annularly circular contact portion is configured to contact the first inner wall surface as the piston is inserted in the first passage. The pair of non-contact portions are configured not to contact the first inner wall surface as the piston is inserted in the first passage, located at both sides of the annularly circular contact portion in a direction of extension of the first imaginary center line and having an outside diameter that is smaller than that of the annularly circular contact portion. The pair of non-contact portions are shaped to be plane-symmetric with respect to a first imaginary surface that includes the annularly circular contact portion and is orthogonal to the first imaginary center line. In the present invention, in particular, the first section of the housing is formed with at least one groove portion communicating with the first passage to discharge air in the first passage when the piston is inserted from the insertion port. The at least one groove portion communicates with the insertion port, and extends along the first imaginary center line. The length of the at least one groove portion along the first imaginary center line and the length of the non-contact portions of the piston are determined such that air in the housing is discharged out of the housing through the at least one groove portion until the piston is inserted into the first passage to the extent that the annularly circular contact portion goes beyond the at least one groove portion. If at least one groove portion is formed as in the present invention, air in the first passage can be guided to the groove portion when the piston is inserted from the insertion port. Consequently, air in the housing can be reliably discharged.

If the piston is provided with the pair of non-contact portions, the piston can be temporarily arranged during insertion. Further, if the pair of non-contact portions are shaped to be plane-symmetric, the piston can be inserted from the insertion port from either non-contact portion side. The area of contact between the piston and the housing is small. Therefore, even if the housing and the piston are each unitarily formed from the same resin material, the piston still can slide smoothly.

Preferably, the pair of non-contact portions each have an annular non-contact surface that is adjacent to the annularly circular contact portion and has a diameter that is 90% or more of that of the first inner wall surface. If the annular non-contact surfaces are formed in this way, the annular non-contact surfaces can be fitted well in the first inner wall surface to reliably temporarily arrange the piston.

The distance between an end portion of the at least one groove portion on the first passage side and an end portion thereof on the first section insertion port side is preferably equal to the distance between an end surface of the piston to be inserted into the first passage and the annularly circular contact portion. Such a configuration allows air to be completely discharged when the piston is completely inserted into the first passage.

The pair of non-contact portions are preferably shaped such that the annularly circular contact portion is positioned at a vertex of an arcuate shape when the piston is cut along a second imaginary surface that includes the first imaginary center line and that is orthogonal to the first imaginary surface. If the pair of non-contact portions are formed in this way, the area of contact between the piston and the housing can be reduced, which allows the viscous material to be pushed out with a small force.

An end portion of each of the pair of non-contact portions is preferably shaped to surface-contact the third inner wall surface surrounding the third passage. If the shape of the end portion of each of the non-contact portions is determined in this way, it is possible to discharge a larger amount of the viscous material.

BRIEF DESCRIPTION OF DRAWINGS

FIG. 3 is a cross-sectional view taken along the line A-A of FIG. 1 with a piston pushed in.

DESCRIPTION OF EMBODIMENTS

An embodiment in which the present invention is applied to a dental viscous material container as a type of a viscous material container will be described below with reference to the drawings.

Figure 1:
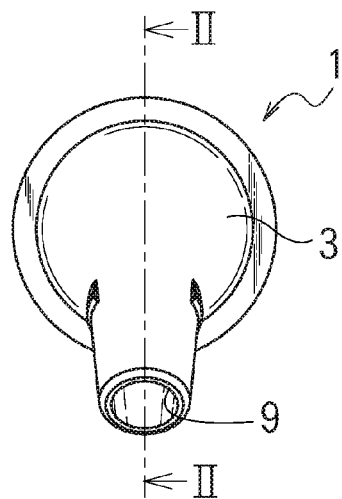
FIG. 1 is a front view of a dental viscous material container as a type of a viscous material container according to an embodiment of the present invention.
Figure 2:
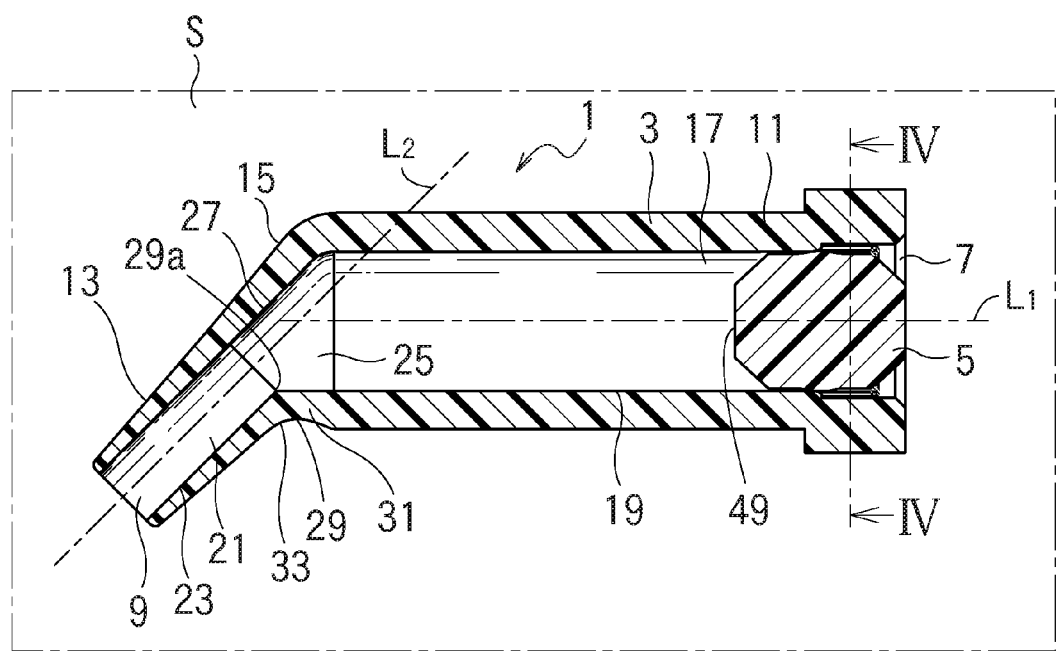
FIG. 2 is a cross-sectional view taken along the line A-A of FIG. 1.
Figure 3:
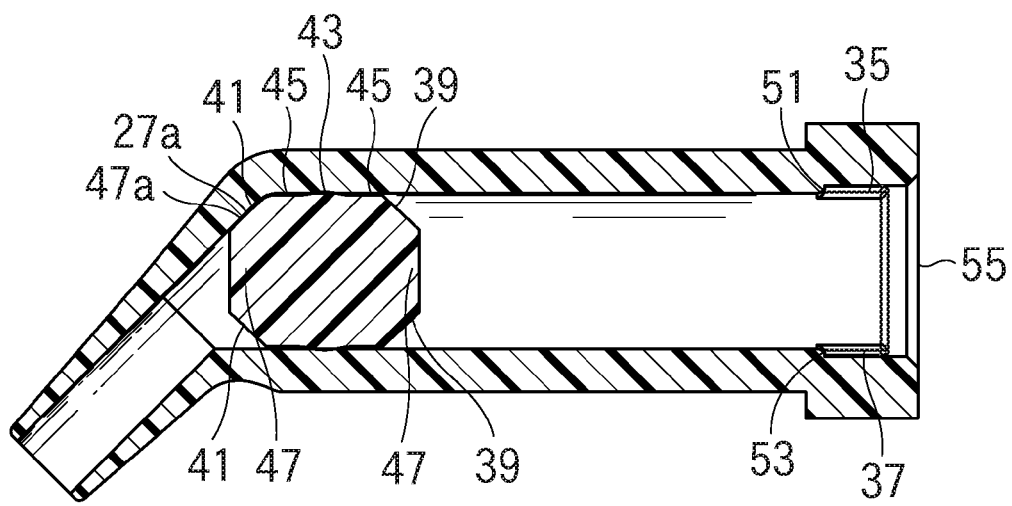
Figure 4:
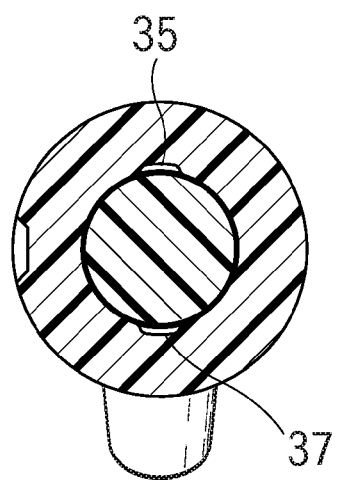
FIG. 4 is a cross-sectional view taken along the line B-B of FIG. 2.

FIG. 1 is a front view of a dental viscous material container 1 according to an embodiment of the present invention. FIG. 2 is a cross-sectional view taken along the line A-A of FIG. 1. FIG. 3 is a cross-sectional view taken along the line A-A of FIG. 1 with a piston pushed in. FIG. 4 is a cross-sectional view taken along the line B-B of FIG. 2. The dental viscous material container 1 has a housing 3 configured to house a dental viscous material (not illustrated) and a piston 5 operable to push out the dental viscous material. The housing 3 and the piston 5 are each unitarily formed from the same resin material. Examples of the resin material include polyethylene, polyacetal, polypropylene, polyamide, vinyl chloride resins, nylon, phenol resins, polyurethane, saturated polyester resins, melamine resins, polyvinylidene chloride, unsaturated polyester resins, polybutadiene, polystyrene, EVA (ethylene-vinyl acetate copolymer) resins, styrol resins, polymethylpentene, methacrylic styrene, ABS (acrylonitrile butadiene styrene) resins, and polycarbonate. In the embodiment, polypropylene is used. The housing 3 is formed using a material that does not transmit visible rays. Consequently, even if a photocurable dental viscous material is housed in the housing 3, it is possible to prevent the dental viscous material from being cured during storage.

The housing 3 includes an insertion port 7 into which the piston 5 is inserted and to which a dedicated pushing device (not illustrated) with a handle is to be connected, and a discharge port 9 from which the dental viscous material is discharged. The housing 3 includes a first section 11 having the insertion port 7 at an end thereof, a second section 13 having the discharge port 9 at an end thereof, and a third section 15 positioned between the first section 11 and the second section 13. The first section 11 includes a first inner wall surface 19 configured to surround a first passage 17 extending along a first imaginary center line L1 from the insertion port 7 and having a transverse sectional shape that is circular about the first imaginary center line L1. The second section 13 includes a second inner wall surface 23 configured to surround a second passage 21 extending along a second imaginary center line L2 from the discharge port 9 and having a transverse sectional shape that is circular about the second imaginary center line L2. The second imaginary center line L2 intersects the first imaginary center line L1. The third section 15 includes a third inner wall surface 27 configured to surround a third passage 25 communicating with the first passage 17 and the second passage 21.

The dental viscous material container 1 also includes a continuous angular portion 29 formed at a boundary portion between the second inner wall surface 23 and the third inner wall surface 27 to extend over a predetermined angular range. The continuous angular portion 29 extends in the circumferential direction with respect to an angular portion 29a located in an imaginary surface S including the first imaginary center line L1 and the second imaginary center line L2. The angular portion 29a has an angle equal to an intersection angle between the first imaginary center line L1 and the second imaginary center line L2.

The first section 11 is formed with two groove portions 35 and 37 communicating with the first passage 17 to discharge air in the first passage 17 when the piston 5 is inserted from the insertion port 7. The two groove portions 35 and 37 communicate with the insertion port 7, and extend along the first imaginary center line L1. The length of the groove portions 35 and 37 along the first imaginary center line L1 and the length of a non-contact portion 39 of the piston 5 to be discussed later are determined such that air in the housing 3 is discharged out of the housing 3 through the groove portions 35 and 37 until the piston 5 is inserted into the first passage 11 to the extent that an annularly circular contact portion 43 of the piston 5 goes beyond the groove portions 35 and 37. If the groove portions 35 and 37 are formed in this way, air in the first passage 17 can be guided to the groove portions 35 and 37 when the piston 5 is inserted from the insertion port 7. Consequently, air in the housing 3 can be reliably discharged. In the embodiment, two groove portions are formed. However, it is a matter of course that one or three or more groove portions may be formed as long as air in the housing 3 can be reliably discharged.

Figure 5:
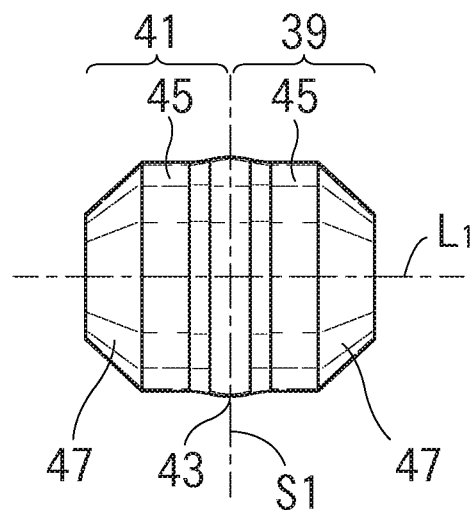
FIG. 5 is a side view of the piston according to the embodiment of the present invention.
Figure 6:
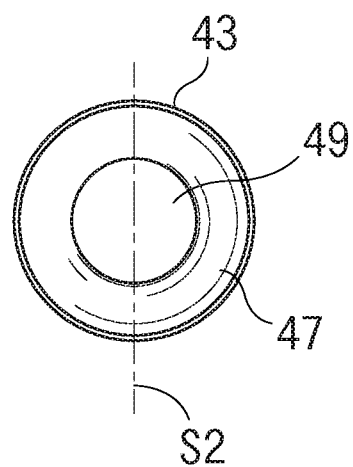
FIG. 6 is a front view of the piston.
Figure 7:
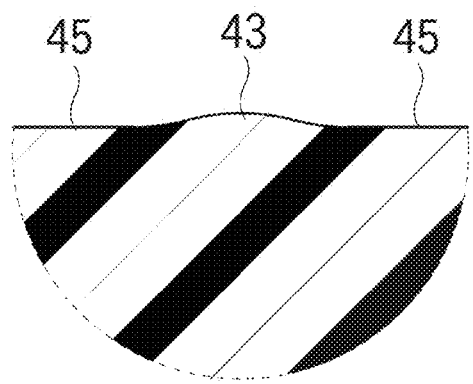
FIG. 7 is a cross-sectional view of the piston taken along a second imaginary surface, illustrating a part of an annularly circular contact portion and the surroundings thereof as enlarged.

Next, the shape of the piston 5 will be described. FIG. 5 is a side view of the piston 5. FIG. 6 is a front view of the piston 5. FIG. 7 is a cross-sectional view of the piston 5 taken along the second imaginary surface S2, illustrating a part of the annularly circular contact portion 43 and the surroundings thereof as enlarged. The piston 5 includes the annularly circular contact portion 43 and a pair of non-contact portions 39 and 41. The annularly circular contact portion 43 contacts the first inner wall surface 19 as the piston 5 is inserted in the first passage 17. The pair of non-contact portions 39 and 41 do not contact the first inner wall surface 19 as the piston 5 is inserted in the first passage 17, located at both sides of the annularly circular contact portion 43 in the direction of extension of the first imaginary center line L1 and having an outside diameter that is smaller than that of the annularly circular contact portion 43. If the piston 5 is provided with the pair of non-contact portions 39 and 41, the piston 5 can be temporarily arranged during insertion. Further, if the pair of non-contact portions 39 and 41 are shaped to be plane-symmetric, the piston 5 can be inserted from the insertion port 7 from either non-contact portion side. The area of contact between the piston 5 and the housing 3 is small. Therefore, even if the housing 3 and the piston 5 are each unitarily formed from the same resin material, the piston 5 still can slide smoothly.

The pair of non-contact portions 39 and 41 each have an annular non-contact surface 45 that is adjacent to the annularly circular contact portion 43. The annular non-contact surface 45 has a diameter that is 90% or more of that of the first inner wall surface 19. If the annular non-contact surfaces 45 are formed in this way, the annular non-contact surfaces 45 can be fitted well in the first inner wall surface 19 to reliably temporarily arrange the piston 5. An end portion 47 of each of the pair of non-contact portions 39 and 41 is shaped to surface-contact the third inner wall surface 27 surrounding the third passage 25. If the shape of the end portion 47 of each of the pair of non-contact portions 39 and 41 is determined in this way, it is possible to discharge a larger amount of the dental viscous material without waste. In the embodiment, the end portion 47 is formed in a truncated conical shape. As illustrated in FIG. 3, a surface 27a of the third inner wall surface 27 on the upper side (the side facing the angular portion 29a) and a conical surface 47a of the end portion 47 on the upper side surface-contact each other with the piston 5 completely pushed toward the discharge port 9.

The distance between an end surface 49 of the piston 5 to be inserted into the first passage 17 and the annularly circular contact portion 43 is equal to the distance between respective end portions 51 and 53 of the groove portions 35 and 37 on the first passage 17 side and an end portion 55 of the first section 11 on the insertion port 7 side. Such a configuration allows air to be completely discharged when the piston 5 is completely inserted into the first passage 17. In addition, the pair of non-contact portions 39 and 41 are shaped such that the annularly circular contact portion 43 is positioned at a vertex of an arcuate shape when the piston 5 is cut along the second imaginary surface S2 which includes the first imaginary center line L1 and which is orthogonal to the first imaginary surface S1. If the pair of non-contact portions 39 and 41 are formed in this way, the area of contact between the piston 5 and the housing 3 can be reduced, which allows the dental viscous material to be pushed out with a small force.

In the embodiment described above, the housing 3 and the piston 5 are formed from the same material. However, it is a matter of course that the housing 3 and the piston 5 may be formed from different materials.

In the embodiment described above, the discharge port 9 is exposed. However, it is a matter of course that the third section 15 may be fitted with a cap configured to block the discharge port 9. In this case, an engagement structure may be provided between the outer peripheral portion of the third section 15 and the cap to prevent the cap from falling off.

INDUSTRIAL APPLICABILITY

According to the present invention, the groove portions are formed to discharge air in the first passage when the piston is inserted from the insertion port. Thus, air in the first passage can be guided to the groove portions when the piston is inserted from the insertion port. As a result, air in the housing can be reliably discharged.

DESCRIPTION OF REFERENCE NUMERALS 1 dental viscous material container
3 housing
5 piston
7 insertion port
9 discharge port
11 first section
13 second section
15 third section
17 first passage
19 first inner wall surface
21 second passage
23 second inner wall surface
25 third passage
27 third inner wall surface
27a surface
29 continuous angular portion
29a angular portion
31 wall portion
33 recessed portion
35, 37 groove portion
39, 41 non-contact portion
43 annularly circular contact portion
45 annular non-contact surface
47 end portion
47a conical surface
49 end surface
51, 53 end portion
55 end portion
L1 first imaginary center line
L2 second imaginary center line
S imaginary surface
S1 first imaginary surface
S2 second imaginary surface

What is claimed is:

1. A viscous material container comprising:
   a housing comprising:
      a first section having an insertion port at an end thereof and including a first inner wall surface configured to surround a first passage extending along a first imaginary center line from the insertion port and having a transverse sectional shape that is circular about the first imaginary center line;
      a second section having a discharge port at an end thereof and including a second inner wall surface configured to surround a second passage extending along a second imaginary center line from the discharge port and having a transverse sectional shape that is circular about the second imaginary center line, the second imaginary center line intersecting the first imaginary center line; and a third section positioned between the first section and the second section and including a third inner wall surface configured to surround a third passage communicating with the first passage and the second passage; and a piston operable to move inside at least the first passage to push out a viscous material, which is contained in at least the first passage, from the discharge port through the second and third passages, the piston comprising:

one annularly circular contact portion configured to contact the first inner wall surface as the piston is inserted in the first passage, and a pair of non-contact portions configured not to contact the first inner wall surface as the piston is inserted in the first passage, located at both sides of the annularly circular contact portion in a direction of extension of the first imaginary center line and having an outside diameter that is smaller than that of the annularly circular contact portion; the pair of non-contact portions being shaped to be plane-symmetric with respect to a first imaginary surface that includes the annularly circular contact portion and is orthogonal to the first imaginary center line, wherein:

the first section of the housing is formed with at least one groove portion communicating with the first passage to discharge air inside the first passage when the piston is inserted from the insertion port;

the at least one groove portion communicates with the insertion port, and extends along the first imaginary center line;

a length of the at least one groove portion along the first imaginary center line and a length of the non-contact portions are determined such that air inside the housing is discharged out of the housing through the at least one groove portion until the piston is inserted into the first passage to the extent that the annularly circular contact portion goes beyond the at least one groove portion;

the pair of non-contact portions each have an annular non-contact surface that is adjacent to the annularly circular contact portion and each have a diameter that is equal to or greater than 90% of a diameter of the first inner wall surface, whereby a gap is defined between the annular non-contact surface of each non-contact portion and the first inner wall surface; and the pair of non-contact portions are shaped such that the annularly circular contact portion is positioned at a vertex of an arcuate shape when the piston is cut along a second imaginary surface that includes the first imaginary center line and that is orthogonal to the first imaginary surface.

2. The viscous material container according to claim 1, wherein an end portion of each of the pair of non-contact portions is shaped such that a part of the end portion of one of the pair of the non-contact portions surface-contacts the third inner wall surface surrounding the third passage.

3. The viscous material container according to claim 1, wherein the housing and the piston are each unitarily formed from the same resin material.

4. The viscous material container according to claim 1, wherein a distance between an end portion of the at least one groove portion on the first passage side and the insertion port is equal to a distance between a leading end surface of the piston to be inserted into the first passage and the annularly circular contact portion, thereby allowing the air to be substantially discharged when the piston is completely inserted into the first passage.

5. The viscous material container according to claim 4, wherein an end portion of each of the pair of non-contact portions is shaped such that a part of the end portion of one of the pair of the non-contact portions surface-contacts the third inner wall surface surrounding the third passage.

* * * * *